US010463251B2

(12) United States Patent
McCafferty

(10) Patent No.: US 10,463,251 B2
(45) Date of Patent: Nov. 5, 2019

(54) OPHTHALMOLOGICAL INSTRUMENT

(71) Applicant: CATS Tonometer, LLC, Tucson, AZ (US)

(72) Inventor: Sean J. McCafferty, Tucson, AZ (US)

(73) Assignee: CATS TONOMETER, LLC, Tucson, AZ (US)

( * ) Notice: Subject to any disclaimer, the term of this patent is extended or adjusted under 35 U.S.C. 154(b) by 0 days.

(21) Appl. No.: 14/012,592

(22) Filed: Aug. 28, 2013

(65) Prior Publication Data

US 2014/0073897 A1    Mar. 13, 2014

Related U.S. Application Data

(60) Provisional application No. 61/699,062, filed on Sep. 10, 2012.

(51) Int. Cl.
*A61B 3/16* (2006.01)
*A61B 3/14* (2006.01)
*A61B 3/10* (2006.01)

(52) U.S. Cl.
CPC . *A61B 3/16* (2013.01); *A61B 3/14* (2013.01)

(58) Field of Classification Search
CPC ................ A61B 3/10; A61B 3/14; A61B 3/16
See application file for complete search history.

(56) References Cited

U.S. PATENT DOCUMENTS

| | | | | |
|---|---|---|---|---|
| 3,070,997 A | * | 1/1963 | Papritz | A61B 3/16 600/405 |
| 3,187,338 A | * | 6/1965 | Neefe | G02C 7/04 351/159.37 |
| 4,523,597 A | * | 6/1985 | Sawa | A61B 3/16 600/405 |
| 4,628,938 A | * | 12/1986 | Lee | A61B 3/16 600/405 |
| 5,070,875 A | * | 12/1991 | Falck | A61B 3/16 600/405 |
| 5,191,365 A | * | 3/1993 | Stoyan | G02C 7/047 351/159.1 |
| 5,619,289 A | * | 4/1997 | Seidner | B29D 11/00086 351/159.47 |
| 2013/0144185 A1 | * | 6/2013 | Fuller | A61B 3/16 600/561 |

* cited by examiner

*Primary Examiner* — Patrick Fernandes
(74) *Attorney, Agent, or Firm* — Yakov Sidorin; Quarles & Brady LLP

(57) ABSTRACT

Ophthalmological device including an applanation tonometer tip having a bi-curved cornea-contacting surface and method of using such device for measurement of intraocular pressure. The cornea-contacting surface includes a first rotationally symmetric portion a curvature of which is substantially adapted to that of a typical cornea and a second rotationally symmetric portion that is peripheral to and adjoining the first portion. In operation, the applanation of the cornea in an area corresponding to the first portion of the cornea-contacting surface is substantially negligible.

13 Claims, 5 Drawing Sheets

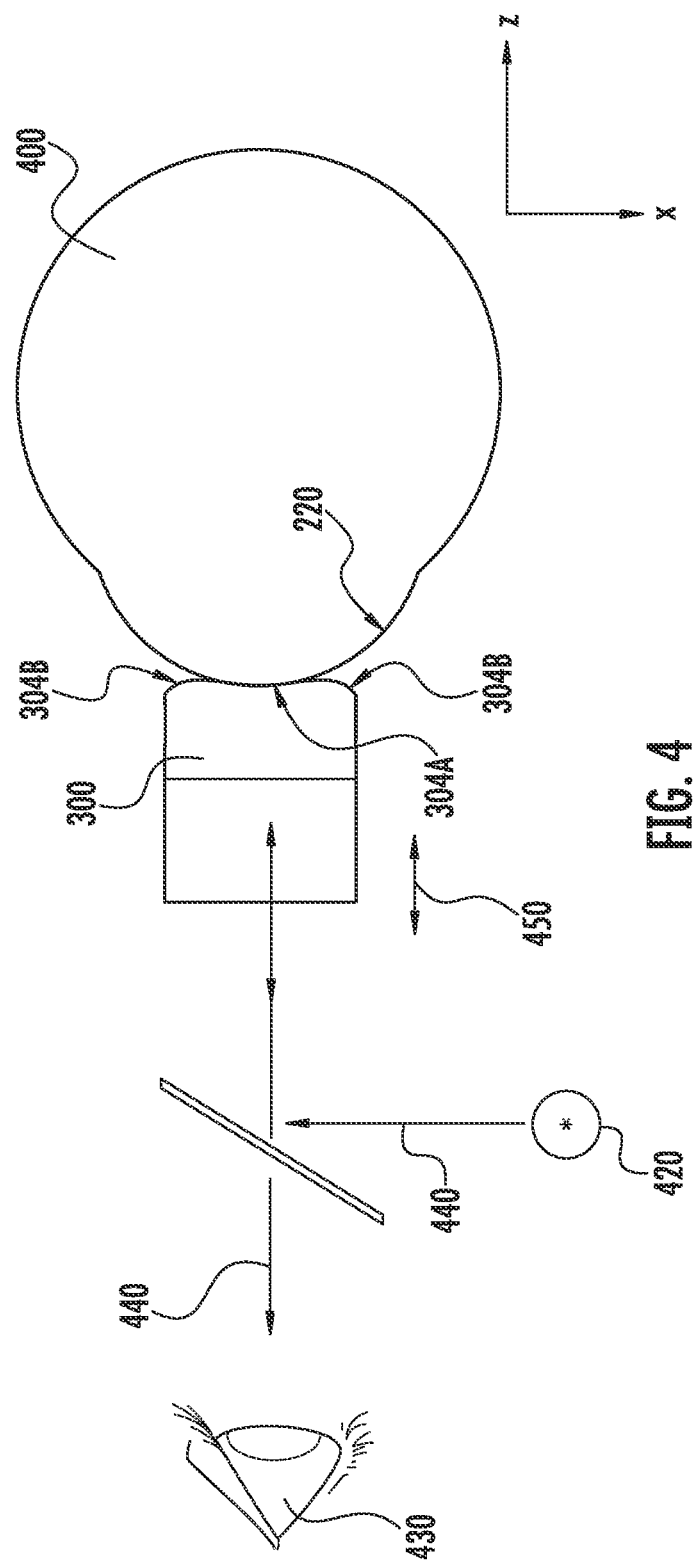

OPHTHALMOLOGICAL INSTRUMENT

CROSS-REFERENCE TO RELATED APPLICATIONS

The present application claims priority and benefit from the U.S. Provisional Patent Application No. 61/699,062 title "Ophthalmological Instrument" as filed on Sep. 10, 2012, which is incorporated herein by reference in its entirety.

TECHNICAL FIELD

The present invention relates to an ophthalmological instrument and, more particularly, to a tip (for applanation tonometer that is structured as a cornea-contacting member) and the applanation tonometer utilizing such tip.

SUMMARY OF THE INVENTION

Embodiments of the present invention provide an ophthalmological instrument comprising a corneal contact member having a front surface that is adapted, in operation, to face the cornea of an eye. The front surface of the corneal contact member includes (i) a corneal contact surface portion having a concave shape, which corneal contact surface portion defines a central portion of the front surface of the corneal contact member; and (ii) a peripheral surface portion surrounding the corneal contact surface portion and tangentially merging with the corneal contact surface portion along a closed plane curve. In one embodiment, curvatures of the peripheral surface portion and the corneal contact surface portion have opposite signs. The concave shape of the corneal contact surface may be approximately adapted to the shape of the cornea such as to establish, in operation, an areal contact (i.e., a contact characterized by an area) between the front surface and the cornea within a bound of the closed plane curve. In a specific embodiment, the closed plane curve defines a circle. The front surface is generally configured to applanate a portion of the cornea when the corneal contact member is pressed, in operation, against the cornea, such that the applanated portion of the cornea defines an annulus around the closed plane curve.

In one embodiment, the corneal contact member is adapted to illuminate and image the cornea of the eye in light passing through the corneal contact member and, in a specific implementation, the corneal contact member is adapted to from a double image of the cornea in light reflected by the cornea. The corneal contact member may be configured as a tip of a Goldmann-type tonometer, with the front surface including a surface that is rotationally symmetric about an axis and having a cross-section that defines a curve having first and second radii of curvature of opposite signs.

In a related implementation, the front surface is devoid of openings therethrough and the peripheral surface portion deviates from a plane. Embodiments of the invention also provide a tonometer including the above-described ophthalmological instrument.

Embodiments of the invention further provide an ophthalmological instrument comprising a corneal contact member having a front surface that is adapted, in operation, to face the cornea of an eye, and that is rotationally symmetric about an axis. Such corneal contact member generally includes (i) a corneal contact surface portion defining a portion of spherical surface that is devoid of openings therethrough, such that the corneal contact surface portion is approximately adapted to the shape of the cornea; and (ii) a peripheral surface portion surrounding the corneal contact surface portion and tangentially merging with the corneal contact surface portion along a closed curve defined in a plane that is perpendicular to the axis. The ophthalmological instrument may be adapted (a) to illuminate and image the cornea in light transmitted through the corneal contact member when this member is brought in contact with the cornea along the corneal contact surface portion. In addition or alternatively, such ophthalmological instrument may be adapted to applanate an annular portion of the cornea when the corneal contact member is pressed against the cornea such as to form contact with the cornea along the corneal contact surface portion, and such as to define the annular portion of the cornea around the above-defined closed curve. In one implementation, the ophthalmological instrument is adapted to maintain a curvature of a portion of the cornea, which is in contact with the corneal contact surface portion, substantially unchanged when the corneal contact member is pressed against the cornea.

Embodiments of the invention further provide a method for measuring intraocular pressure with an applanating tonometer that includes a corneal contact member (which corneal contact member has a corneal contact surface with a shape substantially adapted to a shape of the cornea of an eye). The method includes the steps of (i) pressing the corneal contact surface against the cornea to establish a contact between the corneal contact surface and a first portion of the cornea and to applanate a second portion of the cornea while keeping the curvature of the first portion of the cornea substantially unchanged, such that the second portion defines an annulus around the first portion; and (ii) imaging the cornea in light traversing the corneal contact member to form an image. The method further includes determining a value of the intraocular pressure based on imaging data representing so formed image. In one embodiment, the step of pressing includes pressing a rotationally symmetric surface of the corneal contact member against the cornea. Alternatively or in addition, the step of pressing includes pressing a rotationally symmetric surface having first and second radii of curvature of opposite signs. Alternatively or in addition, the step of pressing includes pressing a surface, of the corneal contact member, that is rotationally symmetric about an axis along which light traverses the corneal contact member to effectuate imaging of cornea. Alternatively or in addition, the step of pressing includes pressing a surface devoid of openings therethrough. The step of imaging may include imaging through a bi-prismatic optical element. In one implementation, the step of determining does not include correction of an offset value caused by a corneal characteristic related to one or more of corneal thickness and corneal stiffness. Generally, an embodiment of the method is devoid of using a pachymeter.

BRIEF DESCRIPTION OF THE DRAWINGS

The invention will be more fully understood by referring to the following Detailed Description of Specific Embodiments in conjunction with the Drawings, of which:

FIG. 4 is a diagram illustrating a method for measurement of intraocular pressure with an embodiment of FIGS. 3A, 3B.

DETAILED DESCRIPTION

The problem of performing the measurement of intraocular pressure with the use of a Goldmann-type tonometer without the need to correct for the contribution of corneal thickness and stiffness is solved with the use a tonometer tip the cornea-contacting surface of which includes a central portion having a concave shape and a peripheral portion encircling the central portion and having a curvature with a sign opposite to the sign of the curvature of the central portion, the central and peripheral portions merging tangentially along a closed plane curve. In accordance with embodiments of the present invention, methods and apparatus are disclosed for an ophthalmological instrument including a corneal contact member for use with the Goldmann tonometer platform. Embodiments of the invention include a tonometer tip that includes a conventionally used biprism-containing portion and a corneal contact surface that is configured to minimize deformation of the corneal surface during the cornea applanation procedure.

Figure 1B:
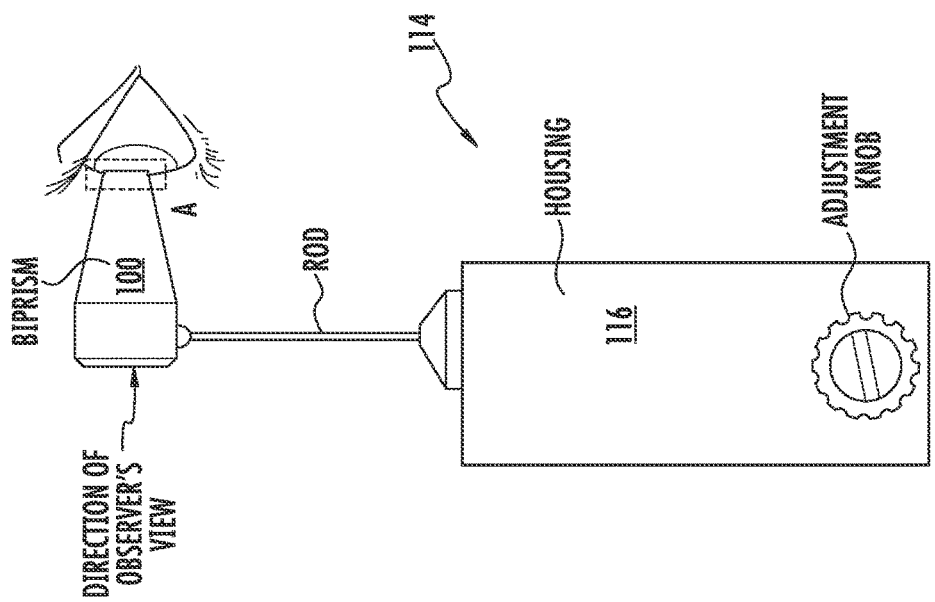
FIG. 1B is a diagram illustrating a Goldmann applanation tonometer.
Figure 1A:
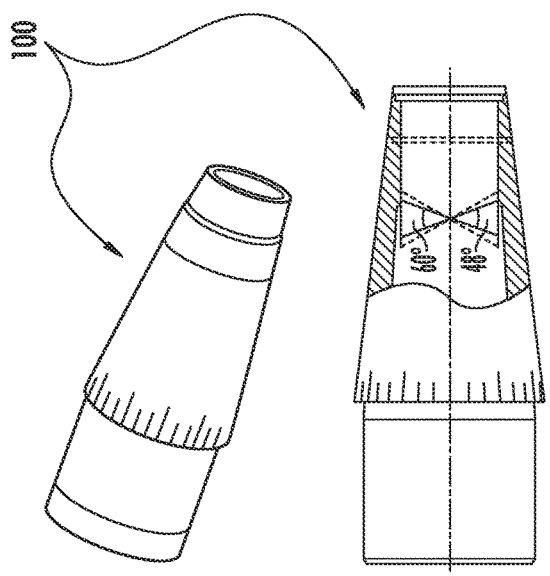
FIG. 1A presents two views of Goldmann applanation tonometer top showing the bi-prism angle for the human (60 degrees)

Tonometry is a non-invasive procedure that eye-care professionals perform to determine the intraocular pressure (IOP), the fluid pressure inside the eye. It is an important test in the evaluation of patients at risk from glaucoma, which may cause visual impairment in a patient. In applanation tonometry the intraocular pressure is inferred from the force required to flatten (applanate) a constant, pre-defined area of the cornea, as per the Imbert-Fick hypothesis that holds that when a flat surface is pressed against a closed sphere with a given internal pressure, an equilibrium will be attained when the force exerted against the spherical surface is balanced by the internal pressure of the sphere exerted over the area of contact. In other words, pressure P within a flexible, elastic (and presumably infinitely thin) sphere is approximately equal to the external force f required to flatten a portion of the sphere, normalized by an area A that is flattened, $P=f/A$. Accordingly, a transparent pressure member with a planar contact surface (such as the element 100 as shown in FIG. 1A, for example) is pressed against the cornea of an eye in such a way that the latter is flattened over a pre-determined area that in practice should be about 7.3 $mm^2$.

Before performing the measurement, and because the pressure member makes contact with the cornea, a topical anesthetic (such as proxymetacaine) is typically introduced on to the surface of the eye (for instance, in the form of eye drops). During the measurement, the eye is illuminated by blue light (delivered from a lamp with a blue filter in front of it, for example). In the zone of contact between the surface of the cornea and the pressure member, the film of tears (which contains fluorescein and has green-yellowish hue when illuminated with the blue light) is displaced, as a result of the contact, so that the boundary between the flattened and the curved areas of the cornea is readily identifiable. The contact pressure required for flattening is used as a measure of intraocular pressure.

Figure 2A:
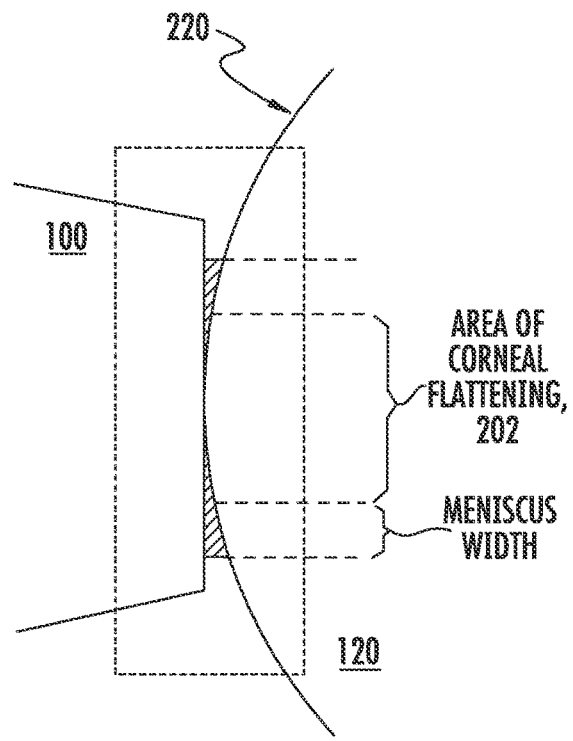
FIG. 2A is a diagram illustrating flattening of the corneal surface due to pressure applied by the tonometer tip.

The classical Goldmann tonometer (see an example 114 in FIG. 1B) has a transparent plastic applanating tip 100 shaped as a truncated cone, through which the surface of cornea 120 is observed with the slit-lamp microscope, and is the most widely used version in current practice of tonometry that utilizes the applanation of the cornea 120. The pressure member, or corneal contact member, also referred to as a tip 100 typically contains a bi-prism (two prisms touching at their apices), which, in reference of FIG. 2A, produces optical doubling of the image of the flattened surface 202 and separates the two image components by a fixed distance or space, across the field of view, that is dependent on the apex angles of the prisms. In further reference to FIG. 1B, the Goldmann tonometer corneal contact member or tip 100 is connected by a lever arm to the tonometer body 116. The tonometer body 116 contains a weight that can be varied.

Figure 2B:
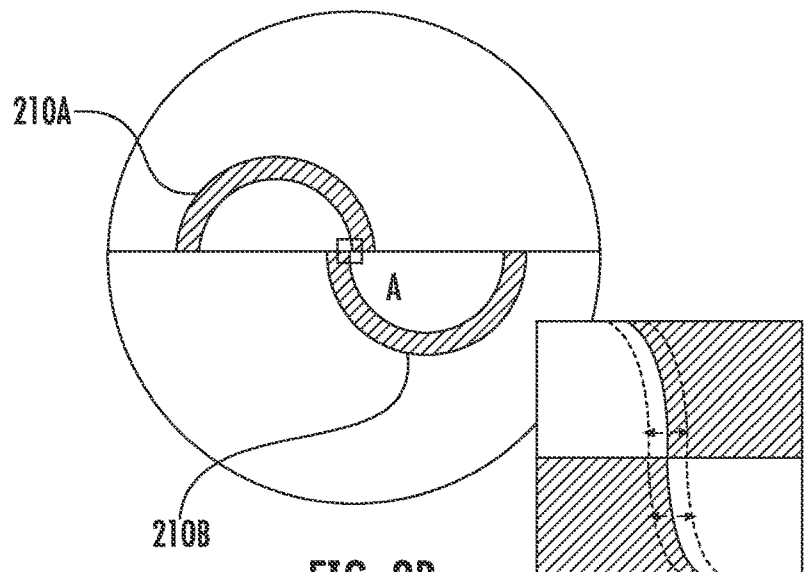
FIG. 2B is a diagram showing the pressure-dependent positioning of two semi-circles representing an image of the flattened portion of the corneal surface.

The observer-examiner uses an optical filter (usually, a cobalt blue filter) to view the two image components (shown as semicircles 210A, 210B in FIG. 2B). The force applied through the tonometer tip 100 to the surface 220 of the cornea 120 is then adjusted using a dial (knob) connected to a variable tension spring of the device until the inner edges of the semicircles 210A, 210B viewed in the viewfinder are made to meet or coincide (see insert of FIG. 2B). Such meeting of the edges occurs when a corneal area of about 3.06 mm in diameter has been flattened and when the two opposing, counteracting forces (the first produced by resistance of the rigid cornea and the second by the tension of the tear film) become substantially equal and cancel each other out, thereby allowing the pressure in the eye to be determined from the force applied.

Like all non-invasive methods, this method of determining an intraocular pressure is inherently imprecise. Some of the measurement errors arise due to the fact that a cornea, unlike the ideal sphere, has non-zero thickness: a thinner than average cornea typically results in an underestimation of the IOP, while a thicker than average cornea may result in an overestimate of the actual IOP. To counterbalance the non-zero stiffness of the cornea and in order to applanate a portion of the cornea, additional force is required that cannot be counted towards the actual value of IOP. The studies revealed a correlation between the corneal thickness and corneal stiffness. Accordingly, to reduce the IOP-measurement error, the value of the initially measured applied force has to be corrected in reference to a second measurement of corneal thickness performed using a pachymeter. The accuracy of such correction is predicated upon the accuracy of correlation between the thickness and stiffness characteristics of the cornea, which is also inherently inaccurate (due to influence of such variable factors as age of the person, a diameter of the cornea, corneal curvature, and effects produced by various eye diseases).

Therefore, a measurement technique and system that increase the precision and accuracy of the IOP results are required. The use of embodiments of the present invention increases the accuracy of the measurement of the IOP with the use of a Goldmann applanation tonometer, thereby eliminating a need in an auxiliary measurement of the corneal thickness and reducing the overall cost of the IOP measurement and increasing the quality of care.

Figure 3A:
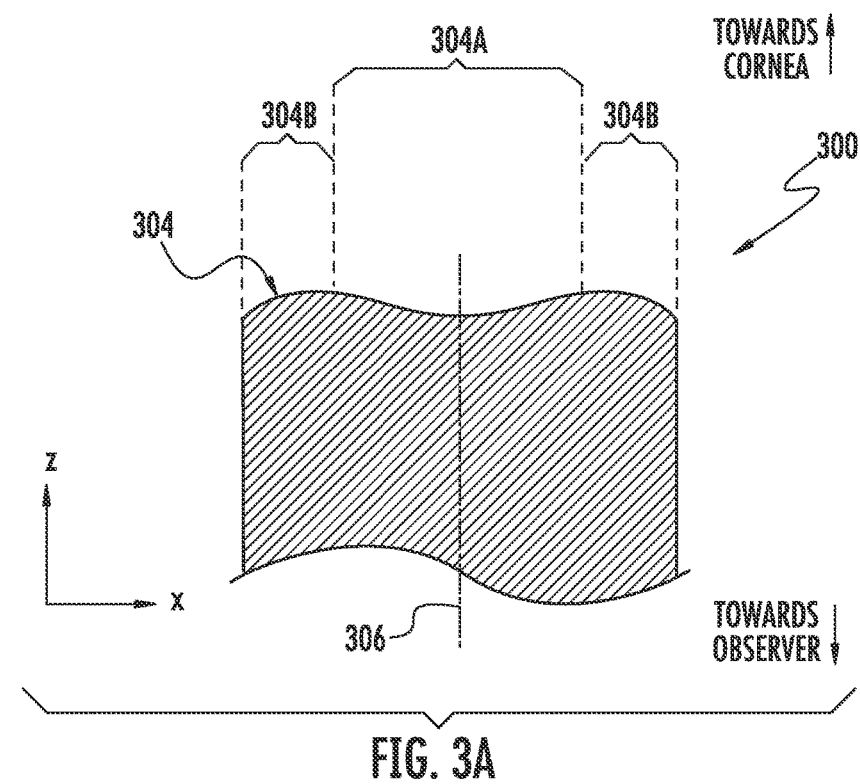
FIGS. 3A and 3B are views that illustrate schematically a tonometer tip according to an embodiment of the invention.
Figure 3B:
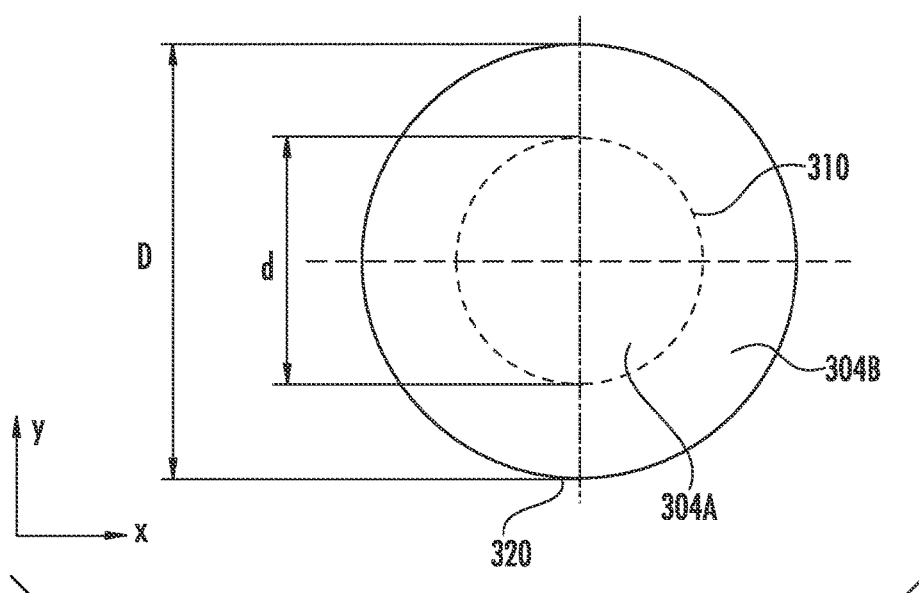

In reference to FIGS. 3A and 3B, a relevant portion 300, representing a tip of an embodiment of an optical element designed to be brought in contact with the cornea of an eye (and referred to as corneal contact member), is shown in a partial cross-sectional view and a front view, respectively. A corneal contact surface 304 includes a central concave surface portion 304A, which is optionally adapted to and is congruent with the curvature of the cornea and which in a specific embodiment may include a surface that is rotationally symmetric about an axis 306. The example of FIGS. 3A and 3B shows just such rotationally symmetric case. In operation, the central concave surface portion 304A is brought in contact with the corneal surface 220. At a periphery of the corneal contact surface 304, the central concave surface portion 304a passes over into a peripheral surface portion 304B that has a curvature of an opposite sign (as compared to that of the central surface portion 304A). The peripheral surface portion 304B defines a looped (and in the specific case—annular) projection, along the axis 306 and onto a plane transverse to the axis 306. The central concave surface portion 304A and the peripheral annular portion 304B are tangentially, seamlessly merging into each other along a closed curve 310 defined in a plane that is tangential to the surface 304 and perpendicular to the axis 306. Put differently, a first plane, which is tangential to the central surface portion 304A at the boundary 310 between the surface portions 304A, 304B and a second plane, which is tangential to the peripheral surface portion 304B at the boundary 310 that is shared by the surface portions 304A, 304B, substantially coincide with one another and do not form a dihedral angle.

In one implementation, and in further reference to FIGS. 3A, 3B, the concave surface portion 304A includes a spherical surface having a radius of curvature R of about −9.0 mm (defined in a plane containing the axis 306), and a footprint or normal projection along the axis 306 with a diameter d of about 3.06 mm (defined in a plane perpendicular to the axis 310). The peripheral annular (i.e., having a form of a ring) surface portion 304B has a radius of curvature of about 3.0 mm (defined in a plane containing the axis 306). In such implementation, the footprint or projection of the corneal contact surface 304 onto the plane normal to the axis 306 defines a circle with a diameter D of about 6.0 mm. The corneal contact surface 304 may include a polymeric surface (for example, polycarbonate, with a refractive index on the order of 1.5) or a glass surface with polished finish of substantially optical quality. Generally, a lateral boundary or perimeter 320 of the surface 304 does not need to meet any particular optical, mechanical, or geometrical requirement.

In a related embodiment, the corneal contact surface is modified such as to have different extents in different directions and, generally, a non-axially-symmetric footprint or normal projection. The central concave surface portion of the corneal contact surface, while remaining substantially fitted (curvature wise) to the corneal surface, may have unequal extents in two (in a specific case—mutually perpendicular) directions. Accordingly, the peripheral surface portion, while remaining adjoining to the central concave surface portion in a fashion described above, also has a ratio of lateral extents that is similar to the ratio characterizing the central concave portion.

Figure 3C:
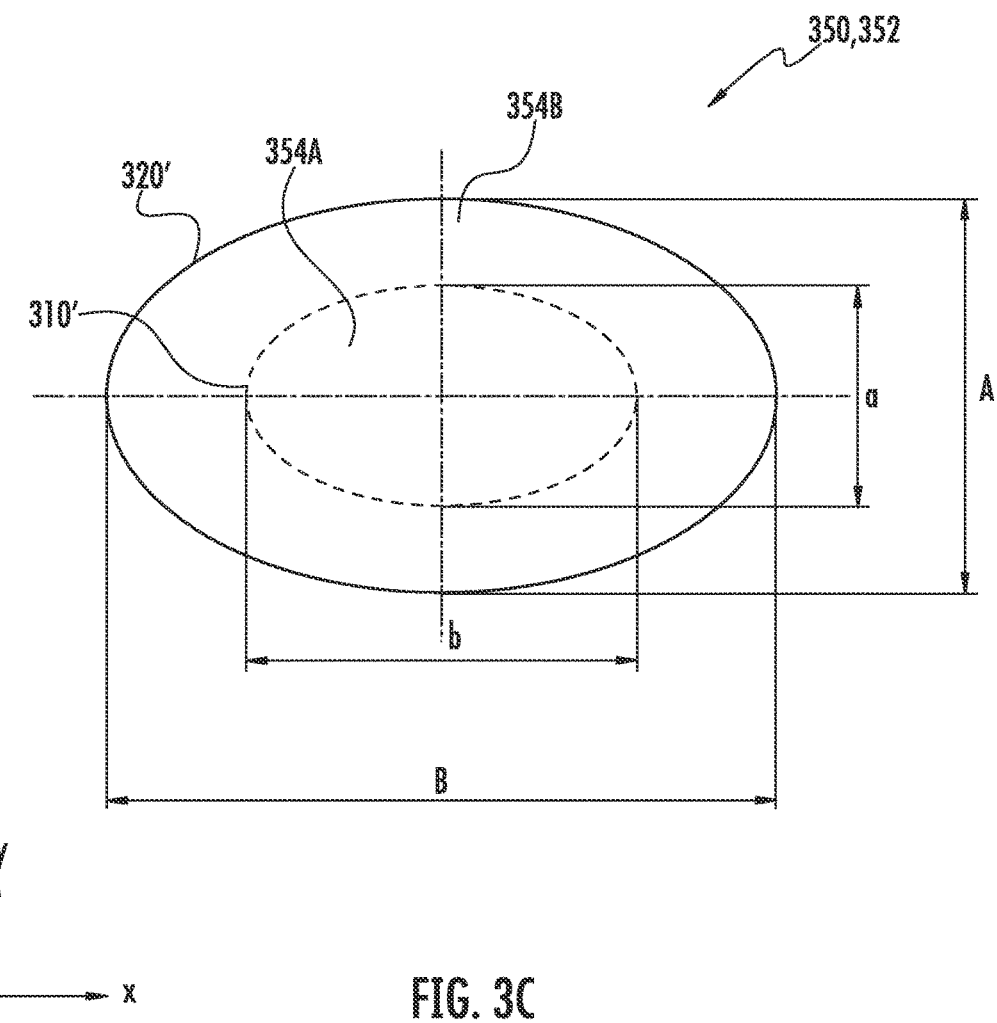
FIG. 3C is a diagram illustrating an alternative embodiment of the invention.

In a specific example shown in FIG. 3C, the so-configured corneal contact surface 350 has an elliptical or oval footprint 352 on a plane that is perpendicular to the z-axis. The surface 350 includes a central, substantially spherical surface portion 354A and a peripheral annular portion 354B, each of which has an elliptically-shaped corresponding projection on the plane that is perpendicular to the axis 306 (which, in FIG. 3C, is parallel to the axis z of the indicated local system of coordinates). As shown, the dimensions of the central surface portion 354A along the minor and major axes of the corresponding footprint are a and b, respectively. The maximum dimensions of the peripheral surface portion 354B along the corresponding minor and major axes of its footprint are A and B, respectively, and indicated by a perimeter 320'. The surface portions 354A, 354B are tangentially, seamlessly merging into one another along an elliptical close plane curve 310' in a fashion similar to that described in reference to FIGS. 3A and 3B. In one implementation, a is about 2.13 mm, b is about 3.06 mm. The bi-prismatic element (not shown) that is internal to the corneal contact member having the surface 350 may be oriented such as to approximately bisect the long extent B of the footprint 352 of FIG. 3C.

The implementation illustrated in FIG. 3C is adapted to facilitate the measurements of the IOP of the patients with interpalpebral features that may not necessarily allow the observer-examiner to accommodate a symmetrically-structured corneal contact surface of the embodiment of FIGS. 3A and 3B. It is appreciated that, when the implementation of the invention the operation of which is represented by FIG. 3C is used in practice, the area of the cornea subject to applanation remains substantially the same as that corresponding to the embodiment of FIG. 3B. The lateral dimension of the oval footprint corresponding to 354A that accommodates a narrow interpalpebral fissue (partially closed lids) is reduced, while the orthogonal dimension of the footprint (along the eye lids) is increased, as compared to the diameter of the footprint 304A. Under some conditions, the force required to achieve applanation may be reduced.

Referring now to FIG. 4, which show schematically the process of the examination of an eye 400, during which a corneal contact member 300 is brought in contact with the corneal surface 220. The corneal contact surface 304, of the member 300, is shaped according to an embodiment of the invention and dimensioned to minimize the deformation of the corneal surface 220 during the applanation procedure with the use of a Goldmann tonometer. In particular, and as will be understood by a skilled artisan, the minimization of the corneal deformation translates to minimization of the contribution of the corneal stiffness into the force defined by the eye in response to the applied measurement of the force (that, in turn, is required for proper applanation of a portion of the corneal surface that defines a circular area with a diameter of about 3.06 mm). As a practical result of such reduction or minimization of the corneal contribution, the correction factor (which takes into account corneal thickness and that is used to practically unreliable compensate for the unknown corneal stiffness, as discussed above) becomes substantially negligible. The computational compensation of the errors of the measurement of the IPO, therefore, becomes practically unnecessary. Similarly, a need to perform costly and time-consuming pachymetries, directed to correcting a cornea-thickness-related error that accompanies conventionally performed measurements of the IPO with the use of the Goldmann tonometer, is substantially eliminated, thereby leading to a measurement method that does not include pachymetry.

Generally, a corneal contact surface of the corneal contact member 300 is structured to include an azimuthally symmetric bi-curved surface having a cross-section (in a plane containing an optical axis of the contact member 300) defined by an axially-symmetric monotonic curve having first and second local maxima, one minimum that coincides with the axis of symmetry of such curve, and a second derivative defined at any point of the curve. Such corneal contact surface includes a central concave portion and a peripheral convex portion that circumscribes the central concave portion. In operation, the central concave portion of the corneal contact surface produces a substantially negligible compression of the central portion of the cornea with which it comes in contact. A region of the corneal contact surface along which the peripheral convex portion and the central contact portion adjoin each other produces a slight corneal compression to define a peripheral ring pattern, observed in form of semicircles, in reflection of light from the cornea.

In further reference to FIG. 4, no particular components of the Goldmann-type tonometer are additionally shown for the simplicity of illustration. The path of light, traversing the bi-prism-containing corneal contact member 300 on its propagation from a light source 420, to a reflecting element 424, to the surface 220 of the cornea (and, in reflection, to an observer 430) is designated with arrows 440. A variable pressure force, applied to the corneal surface 220 is designated with an arrow 450.

It is understood that specific numerical values, chosen for illustration of examples of embodiments described in reference to FIGS. 3A, 3B, and 4, may generally vary over wide ranges to suit different applications. It will be understood by those of ordinary skill in the art that modifications to, and variations of, the illustrated embodiments may be made without departing from the inventive concepts disclosed herein. Both of the central concave surface portion and the associated peripheral surface portion of the corneal contact surface may be uninterrupted and spatially continuous (such as the portions 304A, 304B of FIGS. 3A, 3B or the portions 354A, 354B of FIG. 3C, for example). Alternatively, at least one of the central concave portion and the associate peripheral surface portion may be spatially discontinuous (at least in one direction transverse to the optical axis of the corneal contact member) such as to define, in a projection onto a plane perpendicular to the optical axis of the corneal contact member, a segmented footprint of the corneal contact surface. For example, at least one of the central concave surface portion and the peripheral surface portion may be spatially interrupted such as to preserve symmetry of such interrupted surface portion(s) with respect to at least one spatial axis. In reference to FIGS. 3A, 3B, and as a specific example, the peripheral surface portion 304B may be spatially interrupted along the y-axis. In operation, when pressed against the cornea, such segmented structure will define a plurality of applanation areas that are located substantially symmetrically about an axis around which the surface interruption is present (in this case, along the y-axis).

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

The use of terms "substantially", "approximately", "about" and similar terms in reference to a descriptor of a value, element, or property at hand is intended to emphasize that the value, element, or property referred to, while not necessarily being exactly as stated, would nevertheless be considered, for practical purposes, as stated by a person of skill in the art. As understood by a skilled artisan, the practical deviation of the exact value or characteristic of such value, element, or property from that stated may vary within a range defined by an experimental measurement error that is typical when using a measurement method accepted in the art for such purposes.

In addition, the following disclosure may describe features of the invention with reference to corresponding drawings, in which like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

The invention as recited in claims appended to this disclosure is intended to be assessed in light of the disclosure as a whole, including features disclosed in prior art to which reference is made. Accordingly, the invention should not be viewed as being limited to the disclosed embodiment(s).

What is claimed is:

1. A tonometer tip configured for use with a tonometer, the tonometer tip comprising:
  a body elongated along an axis, the body having a front surface transverse to the axis and dimensioned to contact a cornea of an eye, said front surface including
    a corneal contact surface portion having a first radius in a plane transverse to the axis and having a surface curvature with a first sign, said corneal contact surface portion being configured
      to physically contact the cornea at said surface curvature and
      to deform a portion of the cornea to produce a counterforce applied by the cornea to the body when the body is pressed against the eye along the axis, said corneal contact surface portion defining a central portion of the front surface of the tonometer tip;
    and
    a peripheral surface portion having
      a second radius in said plane, the second radius being greater than the first radius,
      and
      a surface curvature with a second sign, said second sign being opposite to the first sign,
      said peripheral surface portion being co-axial with the corneal contact surface portion, surrounding the corneal contact surface portion, and tangentially merging with said corneal contact surface portion along a closed plane curve.

2. The tonometer tip according to claim 1, wherein the closed plane curve is defined in a plane that is transverse to the axis.

3. The tonometer tip according to claim 1, wherein said tonometer tip includes an optical prismatic element.

4. The tonometer tip according to claim 1, wherein the first sign is equal to a sign of a curvature of a surface of the cornea with which, in operation of the tonometer tip, said corneal contact surface portion is in physical contact.

5. The tonometer tip according to claim 1, wherein the front surface is axially symmetric about said axis.

6. The tonometer tip according to claim 1, wherein the corneal contact surface portion defines a portion of a spherical surface.

7. The tonometer tip according to claim 1, configured as a tonometer tip of a Goldmann applanation tonometer.

8. The tonometer tip according to claim 1, wherein the corneal contact surface portion is defined by a portion of a spherical surface that is devoid of openings therethrough.

9. The tonometer tip according to claim 1, wherein said front surface is dimensioned to keep a curvature of a first portion of the cornea, which is in physical contact with the corneal contact surface portion when said body is pressed against the cornea, substantially unchanged.

10. The tonometer tip according to claim 4, wherein the corneal contact surface portion is dimensioned to be congruent with said cornea.

11. The tonometer tip according to claim 3, wherein the optical prismatic element includes two prisms, a first prism of the two prisms having a first apex, a second prism of the two prisms having a second apex, the first and second apices touching each other.

12. The tonometer tip according to claim 1, wherein said corneal contact surface portion is configured to physically contact the cornea, when the tonometer tip is attached to the eye, at every point of said corneal contact surface portion.

13. The tonometer tip according to claim 1, wherein said front surface is an azimuthally symmetric bi-curved surface having a cross-section, in a plane containing the axis, that is defined by an axially-monotonic curve with a second derivative defined at any point of said curve.

* * * * *